US006902929B1

(12) United States Patent  
Cichutek et al.

(10) Patent No.: US 6,902,929 B1  
(45) Date of Patent: Jun. 7, 2005

(54) RETROVIRAL VECTORS, METHODS FOR THEIR PREPARATION AND THEIR USE FOR GENE TRANSFER INTO CD4-POSITIVE CELLS

(75) Inventors: Klaus Cichutek, Frankfurt (DE); Jorn Stitz, Frankfurt (DE)

(73) Assignee: Bundesrepublik Deutschland last Represented by the President of the Paul-Ehrlich-Instituts, Langen (DE)

( * ) Notice: Subject to any disclaimer, the term of this patent is extended or adjusted under 35 U.S.C. 154(b) by 0 days.

(21) Appl. No.: 09/380,324

(22) PCT Filed: Feb. 27, 1998

(86) PCT No.: PCT/DE98/00593

§ 371 (c)(1),  
(2), (4) Date: Dec. 8, 1999

(87) PCT Pub. No.: WO98/38825

PCT Pub. Date: Sep. 3, 1998

(30) Foreign Application Priority Data

Feb. 27, 1997 (DE) .......................................... 197 07 971  
Feb. 27, 1998 (DE) .......................................... 198 08 438

(51) Int. Cl.[7] .......................... C12N 5/00; C12N 15/00; C12N 5/08; C12N 15/63; A01N 63/00  
(52) U.S. Cl. .................... 435/320.1; 435/325; 435/366; 435/372.3; 435/455; 424/93.2  
(58) Field of Search ............................. 435/320.1, 325, 435/366, 372.3, 455; 514/44; 424/93.2; 536/23.72

(56) References Cited

FOREIGN PATENT DOCUMENTS

| WO | WO 96/17071 | 6/1996 |
|----|-------------|--------|
| WO | WO 96/30533 | 10/1996 |
| WO | WO 98/38325 | 9/1998 |

OTHER PUBLICATIONS

Schnierle et al., "Pseudotyping of murine leukemia virus with the envelope glycoproteins fo HIV generates a retroviral vector with specificity of infection for CD4–expressing cells", Proc. Natl. Acad. Sci. USA, 94:8640–8645, Aug. 1997.*
Mammano et al., "Truncation to the human immunodeficiency virus type 1 envelope glycoprotein allows efficient pseudotyping of Moloney murine leukemia virus particles and gene transfer into CD4+ cells", J. Virol., 71:3341–3345, Apr. 1997.*
Parolin et al., "Analysis in human immunodeficiency virus type 1 vectors of cis–acting sequences that affect gene transfer into human lymphocytes", J. Virol., 68:3888–3895, Jun. 1994.*
Salmons et al., "Construction of retroviral vectors for targeted delivery and expression of therapeutic genes", Leukemia, 9(Suppl.):S53–S60, Oct. 1995.*

Wilk et al., "Retained infectivity and cytopathogenicity of HIV–1 despite truncation of the C–terminal tail of the env gene product", Virology, 189:167–177, Jul. 1992.*
Denesvre et al., "TM domain swapping of murine leukemia virus and human T–cell leukemia virus envelopes confers different infectious abilities despite similar incorporation into virions", J. Virol., 70:4380–4386, Jul. 1996.*
Zingler and Littman, "Truncation fo the cytoplasmic domain of the simian immunodeficiency virus envelope increases env incorporation into particles and fusogenicity and infectivity", J. Virol., 67:2824–2831, May 1993.*
Anderson, "Human gene therapy", Nature, 392(Suppl.):25–30, Apr. 1998.*
Verma and Somia, "Gene therapy–promises, problems and prospects", Nature, 389:239–242, Sep. 1997.*
Hohne, "Truncation of the human immunodeficiency virus–type–2 envelope glycoprotein allows efficient pseudotyping of murine leukemia virus retroviral vector particles", Virology, 261(1):70–78, Aug. 1999.*
Chemical Abstracts, 125:785060b, (1996).
Cosset et al., "High–Titer Packaging . . . Human Serum", *Journal of Virology*, 12:7430–7435, (1995).
Mammano et al., "Truncation of the Human Imunodeficiency . . . into CD4+ Cells", *Journal of Virology*, 71:3341–3345, (1997).
Miller et al., "Targeted Vectors for Gene Therapy", *The FASEB Journal*, 9:190–199, (1995).
Salmons et al., "Construction of Retroviral Vectors . . . Therapeutic Genes", *Lukemia*, 9:S53–S60, (1995).
Takeuchi et al., "Retroviral Pseduotypes . . . Not D–type Retroviruses", *Virology*, 186:792–794 (1992).
Schnierle et al., "Pseudotyping of Murine . . . CD4–expressing cells", *Proc. Natl. Acad. Sci.*, 94:8640–8645, (1997).
von Kalle et al., "Increased Gene Transfer . . . Retroviral Vector", Blood, 84:2890–2897, (1994).
T. Wilk et al., "Retained in Vitro Infectivity and Cytopathogenicity of HIV–1 Despite Truncation of the C–Terminal Tail of the env Gene Product", *Virology*, 189:167–177: (1992).
C. Wilson et al., "Formation of Infectious Hybrid Virions. . . of Moloney Murine Lukemia Virus", *Journal of Virology*, 63(5):2374–2378, (1989).

* cited by examiner

*Primary Examiner*—Joseph T. Woitach  
(74) *Attorney, Agent, or Firm*—Fish & Richardson P.C.

(57) ABSTRACT

The invention relates to the production and use of retroviral vectors for cell specific gene transfer, specially to a production method of retroviral vectors containing capsid particles of murine leukemia virus (MLV) and envelope proteins of human immunodeficiency vises (HIV) or simian immunodeficiency viruses (SIV). Said vectors can be used for gene transfer in selected cell types, specially in CD4-positive mammal cells.

16 Claims, 12 Drawing Sheets

1) Entry

2) Reverse transcription of the expression construct

3) Integration into the genome

4) Synthesis of the therapeutic protein

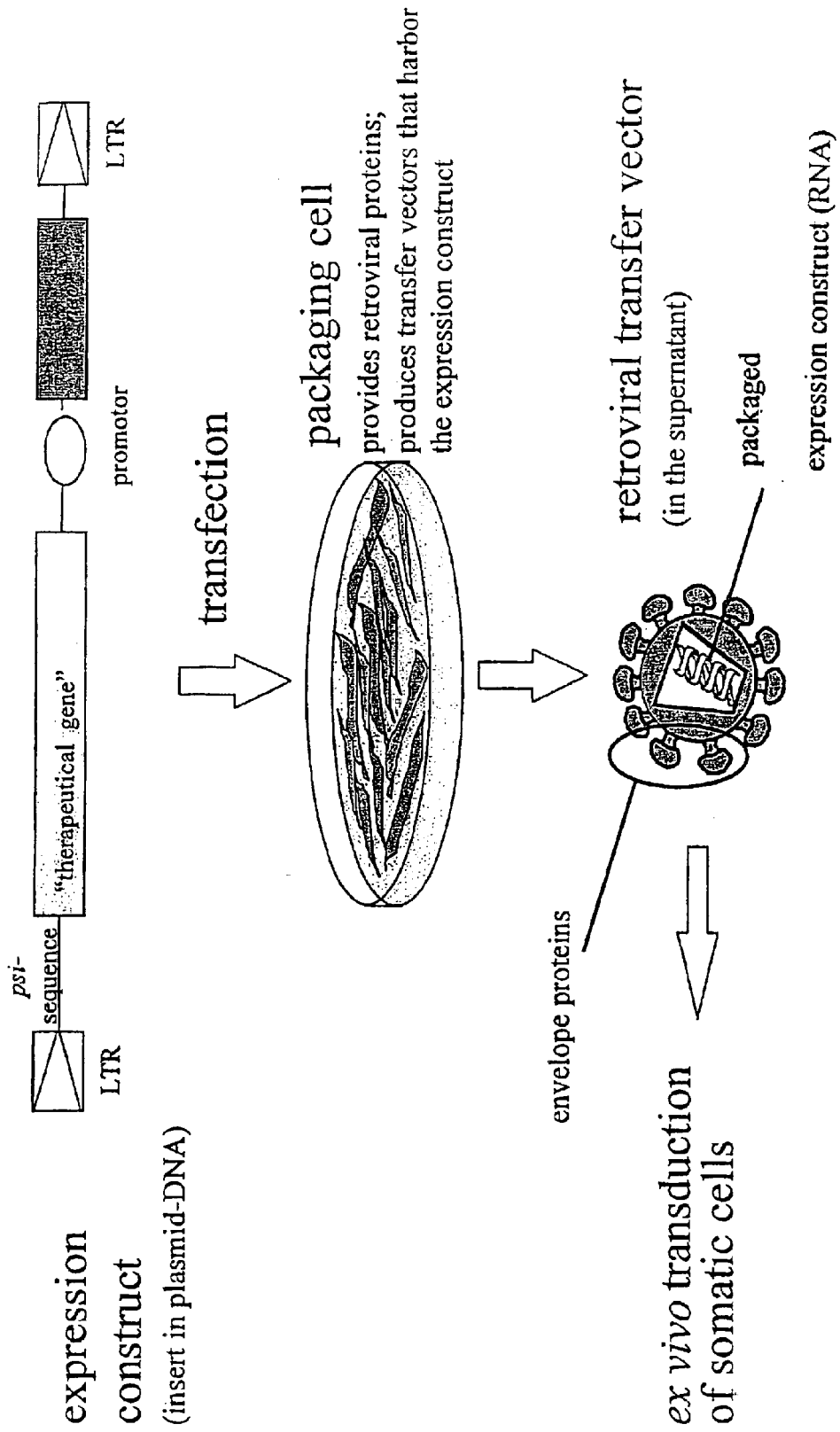

Fig. 4 retroviral packaging cell e.g. TE671 cells: human medullablastom-cells

+

*env* gene variant of HIV-1 expressing a truncated transmembrane protein

Δ gp41-TM fusion-peptide | membrane region (TMR)

↑
stop codon instead of Aminosäure 712

+ expression genes for *gag und pol* of MLV that are not packaged

Blasticidin-resistance gene

+ pMFGInsLacZ expression construct for *lacZ* that is packaged

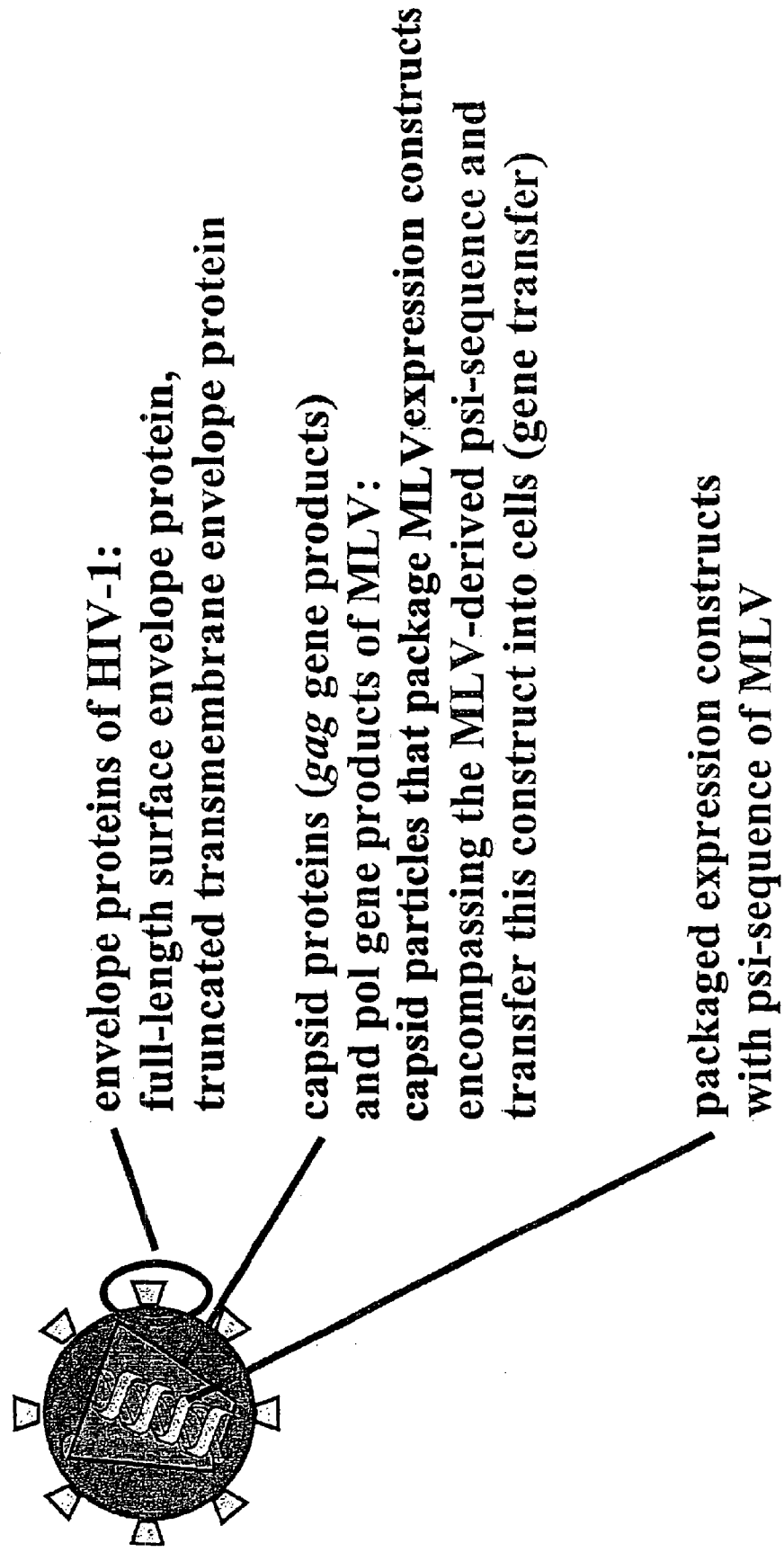
Fig. 5 Assembly of retroviral vectors with foreign envelope proteins of HIV

Fig. 7

MLV *env* from pKA1558

MLV Not 0+ or MLV Not 7+ gp70-SU
p15-TM
*env*
MLV Not

Not I — Not I amplicon of the 3'-region of the MLV *env* gene restriction (Not I) and ligation of the amplicon into the plasmid pRep$\Delta$ *0 env* (Not I) or pRep $\Delta$*7env* (Not I), respectively MLV *env*-region pRep $\Delta$ *0MLV env*
or
pRep $\Delta$ *7MLV env*

Nhe I (5711)  Hind III (6817)  Xho I (8221)

$\Delta$ *0 env*

Not I   Not I

Fig. 8

Nhe AGM ENV+:      Nhe I
5'-CTAGCTAGCATGCCCCTAGGATCAGAAGAAAGAAG-3'

Xho AGM ENV-:      Xho I
5'-CCGCTCGAGCTAATTAAGGATTCCTTCAAGGCC-3'

SIV ENV HIII+:     Hind III
5'-CAAGGCTGAGACAAGCTTGGTGTCACTTCC-3'

Not STOP 0+:       Not I
5'-GTTAGGCAGGGTTACGCGGCCGCTTAACCACAGATCCATATCCACCCG-3'

Not STOP 0-:       Not I
5'-CGGGTGGATATGGATCTGTGGTTAAGCGGCCGCCTAACCCTGCCTAACCC-3'

Not STOP 7+:       Not I
5'-TACTCTCCTCTTTCTCGCGGCCGCTAAATCCACCCGTGGAAGGGACAG-3'

Not STOP 7-:       Not I
5'-TCCCTTCCACGGGTGGATTTAGCGGCCGCGAGAAAGAGGAGAGTAACCCTGCC-3'

Not STOP 16+:      Not I
5'-ATCCACCCGTGGAAGGGCGGCCGCTAAAACGCAGAAGGGCC-3'

Not STOP 16-:      Not I
5'-CCCTTCTGCGTTTTAGCGGCCGCCCTTCCACGGGTGGATATGG-3'

MLV Not 0+:        Not I
5'-AAAAGGAAAAGCGGCCGCTCGATTAGTCCAATTTGTTAAAGACAGGATATCAGTGG-3'

MLV Not 7+:        Not I
5'-AAAAGGAAAAGCGGCCGCGACAGGATATCAGTGGTCCAGGCTCTAGTTTTG-3'

MLV Not-:          Not I
5'-AAAAGGAAAAGCGGCCGCCTATGGCTCGTACTCTATAGGCTTCAGCTGG-3'

Fig. 10

|  | TMR of SIVagm3-TM | C-Terminus |
|---|---|---|
| SIVagm3 wt Env | VLGIIGLRLLYTVYSCIARVRQGY | SPLSPQIHIPWLGQPDNAE.......* <br> 135 aa |
| Δ36 Env | VLGIIGLRLLYTVYSCIARVRQGY | SPLSPQIHIPWLGQPDNAE.......* <br> 36 aa |
| Δ16 Env | VLGIIGLRLLYTVYSCIARVRQGY | SPLSPQIHIPWLGGR * <br> 16 aa |
| Δ7 Env | VLGIIGLRLLYTVYSCIARVRQGY | SPLSRGR * <br> 7 aa |
| Δ0 Env | VLGIIGLRLLYTVYSCIARVRQGY | AAA* <br> 3 aa |
| Δ7MLV Env | VLGIIGLRLLYTVYSCIARVRQGY | SPLSRGRN RISVVQAL* <br> 16 aa |
| Δ0MLV Env | VLGIIGLRLLYTVYSCIARVRQGY | AAARLVQFVKDRISVVQAL * <br> 19 aa |

|  | TMR of MLV | C-Terminus |
|---|---|---|
| MLV wt Env | SPWFTTLISTIMGPLIVLLMILLFGPCILN | RLVQFVKDRISVVQAL* <br> 16 aa |

SEQUENCE LISTING

<160> NUMBER OF SEQ ID NOS: 20

<210> SEQ ID NO 1
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 1
ctagctagca tgcccctagg atcagaagaa agaag                          35

<210> SEQ ID NO 2
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 2
ccgctcgagc taattaagga ttccttcaag gcc                            33

<210> SEQ ID NO 3
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 3
caaggctgag acaagcttgg tgtcacttcc                                30

<210> SEQ ID NO 4
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 4
gttaggcagg gttacgcggc cgcttaacca cagatccata tccacccg            48

<210> SEQ ID NO 5
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 5
cgggtggata tggatctgtg gttaagcggc cgcctaaccc tgcctaaccc          50

<210> SEQ ID NO 6
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 6
tactctcctc tttctcgcgg ccgctaaatc cacccgtgga agggacag            48

<210> SEQ ID NO 7
<211> LENGTH: 53

```
<212> TYPE: DNA
<213> ORGANISM: Artificial Sequence
<220> FEATURE:
<223> OTHER INFORMATION: Synthetic oligonucleotide

<400> SEQUENCE: 7
tcccttccac gggtggattt agcggccgcg agaaagagga gagtaaccct gcc        53

<210> SEQ ID NO 8
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 8
atccacccgt ggaagggcgg ccgctaaaac gcagaagggc c                     41

<210> SEQ ID NO 9
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 9
cccttctgcg ttttagcggc cgcccttcca cgggtggata tgg                   43

<210> SEQ ID NO 10
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 10
aaaaggaaaa gcggccgctc gattagtcca atttgttaaa gacaggatat cagtgg     56

<210> SEQ ID NO 11
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 11
aaaaggaaaa gcggccgcga caggatatca gtggtccagg ctctagtttt g          51

<210> SEQ ID NO 12
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 12
aaaaggaaaa gcggccgcct atggctcgta ctctataggc ttcagctgg             49

<210> SEQ ID NO 13
<211> LENGTH: 24
<212> TYPE: PRT
<213> ORGANISM: Homo sapiens

<400> SEQUENCE: 13

Val Leu Gly Ile Ile Gly Leu Arg Leu Leu Tyr Thr Val Tyr Ser Cys
1               5                   10                  15
```

Ile Ala Arg Val Arg Gln Gly Tyr
            20

<210> SEQ ID NO 14
<211> LENGTH: 19
<212> TYPE: PRT
<213> ORGANISM: Homo sapiens

<400> SEQUENCE: 14

Ser Pro Leu Ser Pro Gln Ile His Ile Pro Trp Leu Gly Gln Pro Asp
1               5                   10                  15

Asn Ala Glu

<210> SEQ ID NO 15
<211> LENGTH: 15
<212> TYPE: PRT
<213> ORGANISM: Homo sapiens

<400> SEQUENCE: 15

Ser Pro Leu Ser Pro Gln Ile His Ile Pro Trp Leu Gly Gly Arg
1               5                   10                  15

<210> SEQ ID NO 16
<211> LENGTH: 7
<212> TYPE: PRT
<213> ORGANISM: Homo sapiens

<400> SEQUENCE: 16

Ser Pro Leu Ser Arg Gly Arg
1               5

<210> SEQ ID NO 17
<211> LENGTH: 16
<212> TYPE: PRT
<213> ORGANISM: Homo sapiens

<400> SEQUENCE: 17

Ser Pro Leu Ser Arg Gly Arg Asn Arg Ile Ser Val Val Gln Ala Leu
1               5                   10                  15

<210> SEQ ID NO 18
<211> LENGTH: 19
<212> TYPE: PRT
<213> ORGANISM: Homo sapiens

<400> SEQUENCE: 18

Ala Ala Ala Arg Leu Val Gln Phe Val Lys Asp Arg Ile Ser Val Val
1               5                   10                  15

Gln Ala Leu

<210> SEQ ID NO 19
<211> LENGTH: 30
<212> TYPE: PRT
<213> ORGANISM: Mus musculus

<400> SEQUENCE: 19

Ser Pro Trp Phe Thr Thr Leu Ile Ser Thr Ile Met Gly Pro Leu Ile
1               5                   10                  15

Val Leu Leu Met Ile Leu Leu Phe Gly Pro Cys Ile Leu Asn
            20                  25                  30

<210> SEQ ID NO 20

```
<211> LENGTH: 16
<212> TYPE: PRT
<213> ORGANISM: Mus musculus

<400> SEQUENCE: 20

Arg Leu Val Gln Phe Val Lys Asp Arg Ile Ser Val Val Gln Ala Leu
1               5                   10                  15
```

RETROVIRAL VECTORS, METHODS FOR THEIR PREPARATION AND THEIR USE FOR GENE TRANSFER INTO CD4-POSITIVE CELLS

This is a continuation of International Patent Application No. PCT/DE98/00593, with an international filing date of 27 Feb. 1998, now pending.

Field of the Invention

The present invention relates to retroviral vectors (cell targeting vectors), methods for their preparation and their use for the gene transfer into CD4-positive cells.

BACKGROUND OF THE INVENTION

The term "retroviral vectors" or "retroviral transfervectors" refers to infectious but replication incompetent retroviruses, which are able to transfer genes as retroviral expression constructs (also designated as "expression vectors") into cells. The gene transfer results in the integration of the expression construct into the genome of the cell. Retroviral gene transfer is advantageous, because (1) usually one copy of the gene of interest is transferred into cells, (ii) the gene generally is transferred without any mutations or recombination and (iii) stable chromosomal integration occurs.

It is known to use retroviral vectors derived from the amphotropic murine leukemia virus (MLV) to transfer certain genes into mammalian cells, especially human cells. These vectors are replication incompetent and run only through one cycle of replication. For the preparation of such vectors two components are required. On the one hand, a packaging cell is required, that provides the gag-, pol- and env-gene products of MLV upon expression of psi-negative constructs so that these genes can not be packaged into a retrovirus. "psi" designates the packaging signal of retroviruses, that mediates efficient packaging of messenger RNA. On the other hand, a so called expression construct has to be generated, that allows packaging into the retroviral vector and transfer by the retrovirus and that encompasses a coding and translatable region of the desired gene product. Thus, the expression construct has to contain the packaging signal "psi". The genes gag-, pol and env within the untreated packaging cell must be psi-negative to prevent the respective messenger RNA from being packaged into retroviral particles. Upon transfer of the expression construct by transfection of the respective vector-DNA into the packaging cells, retroviral vector particles are released into the cell culture supernatant, that exclusively contain the expression construct, but not the psi-negative gag-, pol and env genes, which are thus not transferred into the target cells.

The tropism of retroviral vectors, i.e. the selection of mammalian cells into which these retroviral vectors can transfer the expression construct, is determined by the env gene in the respective packaging cell. The env gene is translated into envelope proteins; the transmembrane protein (TM) and the surface envelope protein (SU), which together form the outer envelope of the retroviral vector particle. The env gene products of the amphotropic MLV, which is widely used for gene transfer, mediate gene transfer into a variety of different mammalian cells. However, in particular for gene transfer into human cells the amphotropic retroviral vector does not allow specific gene transfer into selected human or other mammalian tissues or cell species, as the acceptor protein (receptor) for the amphotropic MLV-envelope proteins which mediates the uptake of amphotropic retroviral vector particles, and the gene transfer is found on the surface of almost all mammalian cells.

In gene therapy, today, stable transfer of different genes is mostly performed in cell culture, i.e. "ex vivo". Retroviral vectors were improved by exchanging the retroviral env gene of MLV within the packaging cells by env genes derived from other viruses. As an example the env gene of MLV has been exchanged by the env gene encoding the protein G of "vesicular stomatitis virus (VSV)" (Burns et al., Proc. Natl Acad. Sci. USA 90 (1993), 8033–8037). The resulting retroviral vectors are characterized by enhanced stability. In WO 96/17071 retroviral vectors are described, that harbor the env gene of "human spuma retrovirus" (HSRV) instead of the MLV env gene. As amphotropic MLV, HSRV does not reveal any specificity for the infection of cells. All mammalian cells that have been tested yet, are permissive for HSRV, independent from which donor species or tissue type they have been derived from (Schweizer et al., J. Virol 71 (1997), 4821–4824, and Russel et al, J. Virol. 70 (1996), 217–222). The possible use of the env genes of "simian sarcoma associated virus" (Takeuchi et al., Virology 186 (1992), 792–794), of the "feline leukemia virus subgroup B" (Porter et al., Hum. Gene Ther. 7 (1996), 913–919), of the "feline endogenous virus RD 14" (Cosset et al., J. Virol. 69 (1995), 7430–7436) and of the "human T-cell leukemia virus I (HTLV-I)" (Vile et al., Virology 180 (1991), 420–424) is suggested in certain experiments. Attempts to prepare retroviral vectors containing the env genes of the *lentiviruses* HIV-1, HIV-2 or "simian immunodeficiency virus (SIV)" have not been successful, yet. Such retroviral vectors would contain the capsid proteins encoded by the gag gene of MLV and the envelope proteins, encoded by the env gene of other retroviruses like HIV or SIV.

Vectors for the specific gene transfer into CD4-positive mammalian cells do not exist, yet.

Summary of the invention

One object of the present invention is to provide retroviral vectors that do not target the amphotropic receptor of mammalian cells, but receptors that are exlusively expressed in certain tissues or cell types. These vectors are suitable to mediate the gene transfer in specific cell types of mammalian origin. It is a further object of the present invention to develop a method to prepare such retroviral vectors.

These objects are solved according to the present invention by providing retroviral vectors comprising the viral cores derived from murine leukemia virus (MLV) and the viral envelopes derived from human immunodeficiency viruses (HIV) or simian immunodeficiency viruses (SIV). In particular, these retroviral vectors are characterized by the use of viral envelopes derived from human immunodeficiency virus type 1 or type 2 (HIV-1 or HIV-2) or from simian immunodeficiency virus (for example: Cerecopithecus aethiops (SIVagm), Macaca mulatta (SIVmac), Pan troglodydytes (SIVcpz), Cerecopithecus mitis (SIVsyk), Papio sphinx (SIVmnd), Cercocebus atys (SIVsm) or Macaca nemestrina (SIVmne)). Preferred are retroviral vectors bearing viral envelopes that contain the full-length surface envelope protein and a truncated form of the transmembrane envelope protein. Particularly preferred are retroviral vectors bearing viral envelopes that contain the full-length surface envelope protein and a truncated form of the transmembrane envelope protein that is elongated by the C-terminus or any other fragment derived from the transmembrane protein of the murine leukemia virus (MLV) or an other virus. Furthermore, packaging cells are provided that express the psi-negative envelope genes (env) of the *lentiviruses* HIV or SIV and the psi-negative gag/pol genes of MLV. In addition, these packaging cells contain psi-positive expression constructs that are transferred by the retroviral vectors according to the present invention.

In one embodiment of this invention viral core particles that are derived from a certain retrovirus can, in connection with expression constructs, be employed for the preparation of viral vectors. These expression constructs, as they contain the packaging signal psi are packaged into the core particles. The core particles containing the expression constructs to be transferred are enveloped by foreign envelopes derived from other virus species or from another cell. The transfer of these expression constructs is then mediated by the retroviral vectors. The incorporation of the foreign virus envelope can for example be mediated by the employment of the preferably truncated variant of the transmembrane envelope protein of HIV-1 env gene pTr712. Furthermore, the incorporation of a foreign viral envelope can be mediated for example by the use of the truncated variant of the transmembrane envelope protein of SIVagm3 env gene Δ0env. In a further embodiment of the present invention full-length transmembrane proteins or transmembrane proteins modified by the fusion of the C-terminus of the transmembrane envelope protein of MLV or the C-termini of the transmembrane envelope proteins of other viruses to the truncated or full-length transmembrane proteins can be used. These modified envelope proteins can be incorporated in retroviral vectors. Especially preferred are vectors derived from MLV that contain the envelope proteins of other retroviruses, in particular of *lentiviruses* like HIV or SIV. These vectors infect the desired cell type by the interaction with the cellular receptor of the virus from which the foreign envelope is derived from.

In another embodiment of the invention any cell is transfected with a psi-negative expression gene encompassing gag/pol genes. Furthermore, the cell can be transfected with a psi-positive expression construct encoding the genetic information intended to be transferred. In addition, this cell is then transfected with a further expression gene encoding foreign envelope proteins. Cell lines constructed this way then generate retroviral vectors that contain the genetic information desired to be transferred.

In a preferred embodiment of the invention, the MLV-env-negative packaging cell line TELCeB6 (Cosset et al., *J. Virol.* 69 (1995), 7430–7436) is transfected with the truncated variant of the HIV-1 env gene pTr712 of plasmid pLβAc/env-Tr712-neo (Wilk et al., *Virology* 189 (1992), 167–177; Krausslich et al., *Virology* 192 (1993) 605–617). The resulting packaging cell line produces retroviral vectors of the type MLV(HIV-1), according to the invention, into the cell culture supernatant. These vectors contain core particles that are produced upon the expression of the gag/pol gene of MLV in this cell and envelope proteins derived from HIV-1 that are intracellularly expressed from the truncated variant of the HIV-L env gene Tr712 and subsequently incorporated into the vector particles. The vectors of the invention contain the full-length surface envelope protein gp 120-SU of HIV-1 and the truncated variant of the transmembrane envelope protein which results from a stop codon at position 712. It was shown in detail that this results in the generation of retroviral vectors for selective transfer of genes into CD4-positive mammalian cells. CD4-positive, but not CD4-negative cells derived from otherwise identical cell lines were selectively transduced by these vectors, i.e. the expression construct gene was transferred. The transduction was inhibited in the presence of antibodies that also inhibit infection by HIV. The surface envelope protein of HIV was detectable on the surface of the generated gene transfer vectors.

In another preferred embodiment of the invention the MLV-env negative packaging cell line TELCeB6 is transfected with the truncated variant of the SIVagm3 env gene Δ0env. The resulting packaging cell line secretes retroviral vectors of the type MLV(SIVagm3) of the present invention into the culture supernatant. These vectors also contain core particles derived from MLV and envelope proteins derived from SIVagm3 that are intracellularly expressed from the truncated variant of the SIVagm3 env gene Δ0env and subsequently incorporated into the vector particles.

Thus, the present invention offers the following possibilities:

- to selectively transfer genes into CD4-positive cells,
- to further optimize efficiency of gene transfer by improving the env gene constructs in comparable packaging cells,
- to develop gene therapy strategies which require or are improved by the selective gene transfer into CD4-positive cells,
- to especially develop gene therapy strategies for the prevention or therapy of HIV-infection in humans by transferring HIV-inhibiting genes e.g. antisense genes, RNA-decoys, transdominat-negative mutant genes of HIV or other *lentiviruses* into CD4-positive cells,
- to especially develop gene therapy strategies to transfer genes into CD4-positive cells for the prevention and treatment of congenital genetic disorders like ADA-deficiency or other genetically treatable diseases that would benefit from the specific gene transfer into certain cells, and
- to study the cellular entry of *lentiviruses* into mammalian cells in detail.

BRIEF DESCRIPTION OF THE DRAWINGS

The figures illustrate the invention.

FIG. 1 shows the principle of retroviral vector mediated gene transfer into mammalian cells.

FIG. 2 shows a scheme of the preparation of a retroviral vector (taken from: "Molecular Biotechnology, Principles and Applications of Recombinant DNA, B. R. Glick and J. J. Pasternak, ASM Press, Washington, D.C., 1994, Page 411, translated into German).

FIG. 3 shows schematically a general method for the preparation of retroviral vectors (retroviral transfer vectors) by transfection of a -expression construct-negative packaging cell line with an expression construct that is due to the presence of a packaging signal (here: psi) able to package a gene to be transferred. (therapeutical effective gene) of interest into retroviral vectors.

FIG. 4 shows a particular method for the preparation of retroviral vectors of the type MLV(HIV-1). The MLV gag/pol expression gene and the psi-positive expression construct pMFGlnsLacZ that are expressed in the env-negative packaging cell line TELCeB6 are shown. In addition, the env gene variant of HIV-1 (Tr712) encoding the full-length surface envelope protein gp120-SU and the truncated variant of the transmembrane envelope protein (Δgp41-TM) are also expressed in this cell line to generate MLV(HIV-1) vectors.

FIG. 5 shows the general assembly of retroviral vectors that consist of core particles from a certain virus in combination with viral envelopes derived from foreign viruses, here explained on the example of MLV(HIV-1) vectors.

FIG. 6 schematically shows the cloning strategy for the generation of SIVagm3 env-expression construct pRep wt env and for the truncated env-genes, here shown at the example of variant Δ0env.

FIG. 7 shows the cloning scheme for the generation of chimeric SIVagm3 env genes Δ0MLVenv and Δ7MLVenv.

FIG. 8 shows the nucleic acid sequences of the oligo-nucleotides used for the cloning of the SIVagm3 env expression constructs (top to bottom SEQ ID NOs:1–12). The nucleic acid sequences of the restriction sites are underlined.

FIG. 10 shows the amino acid sequences of the intracellular domains of the gene products of the SIVagm3 derived env-constructs. The sequences of the SIVagm3 (SEQ ID NOs:13–18) and MLV (SEQ ID NOs:19 and 20) are given for comparison. The amino acids are indicated in the one letter code. Amino acid residues derived from MLV are underlined. The numbers in the designation of the constructs indicate the N-terminal amino acid moieties following the transmembrane region before the stop codons inserted by recombinant PCR. Due to the insertion of a Not I-restriction site two or three amino acids are generated that do not occur in the native SIVagm3 sequence. These amino acid moieties are typed in bold letters. " . . . " designates amino acid moieties of SIVagm3 that are not indicated in detail. "*" indicates the C-terminus of the proteins. The length of the intracellular domains is indicated. "aa" stands for amino acid moieties. "TMR" stands for transmembrane region. The designation "MLV" stands for the 3'-inserted sequences derived from MLV env gene. The inserted C-termini of MLV contain the so called p2-protein (consisting of 16 aa) that is intracellularly cleaved by proteolysis before the envelope proteins are incorporated into the virions.

Figure 1:
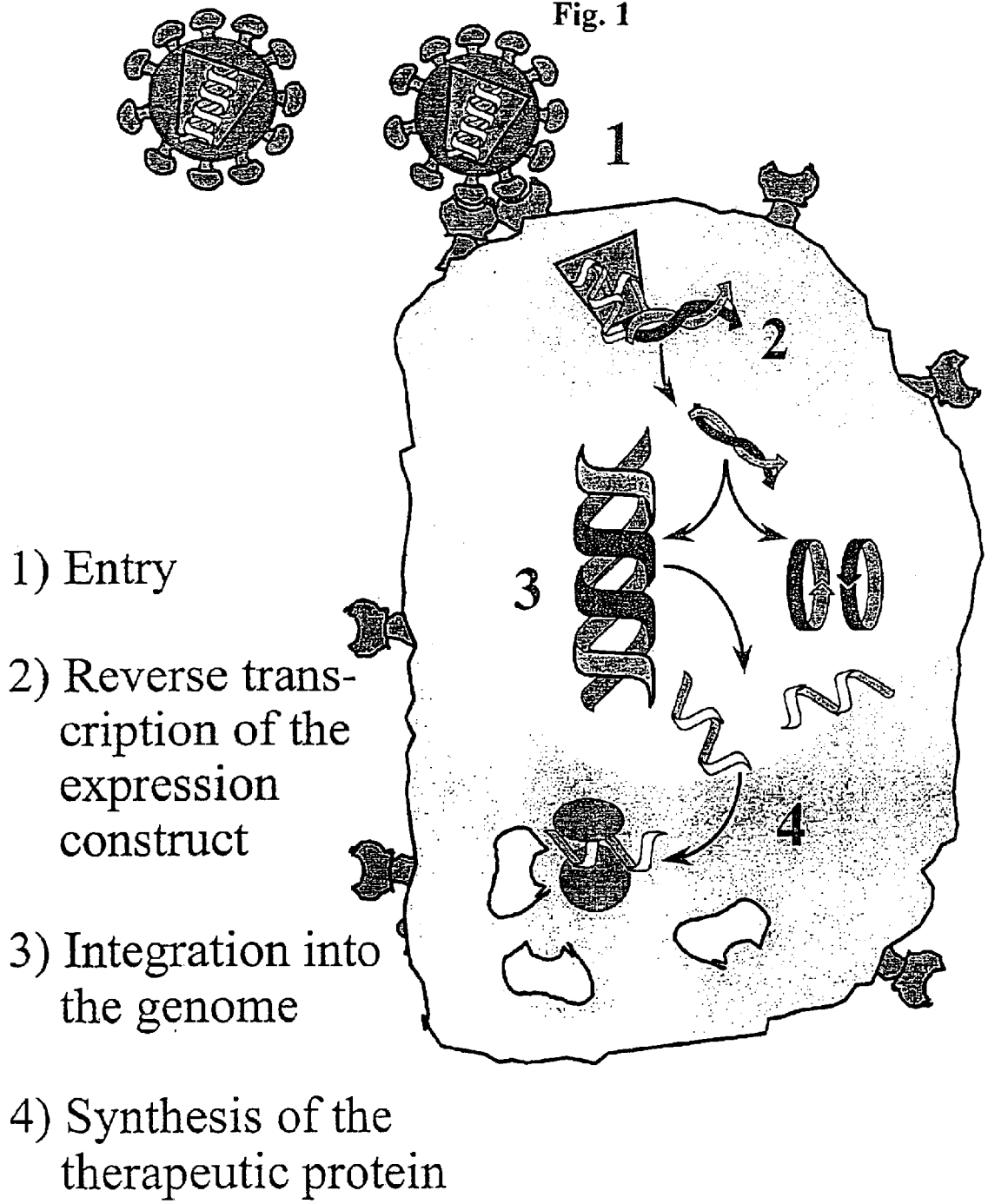
Figure 2:
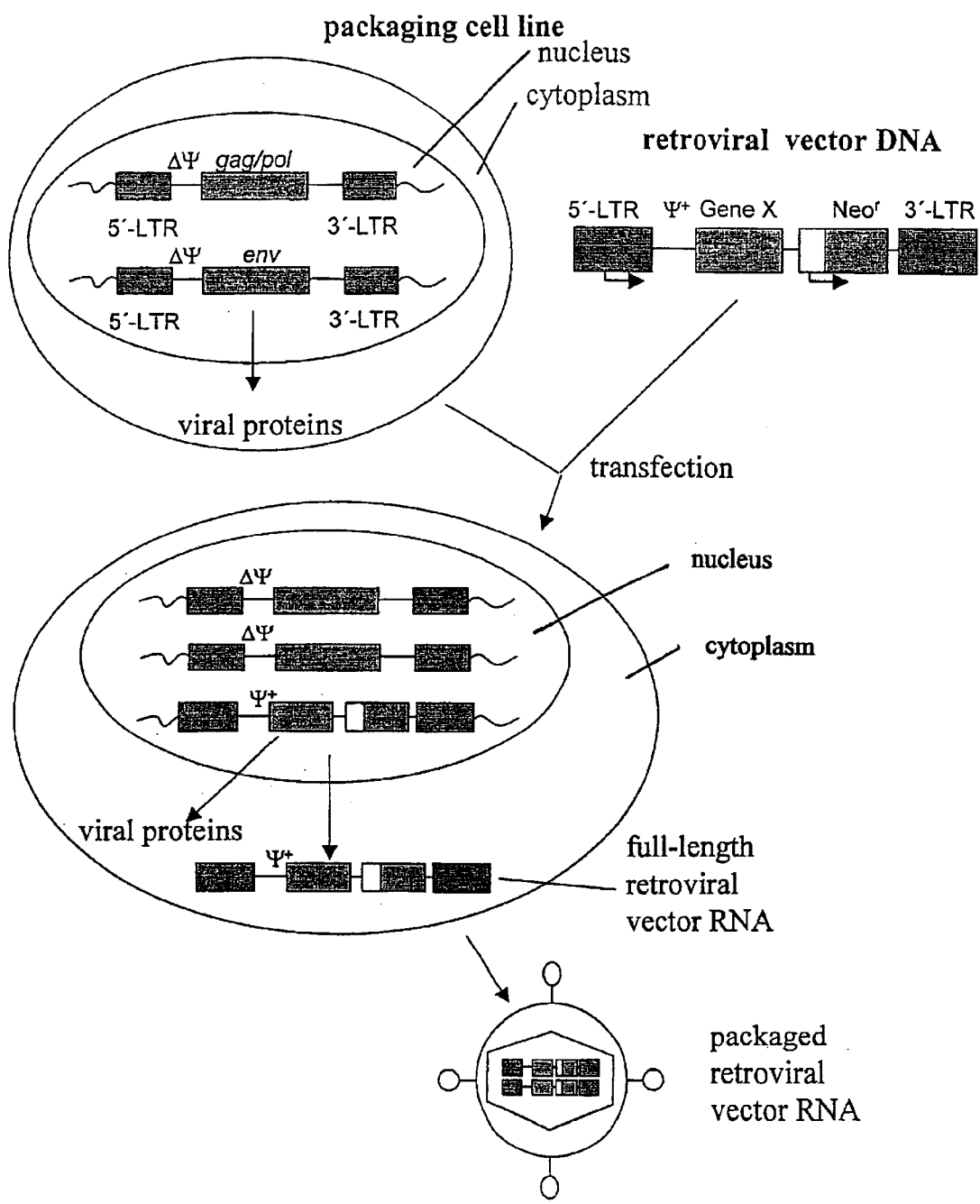
Figure 6:
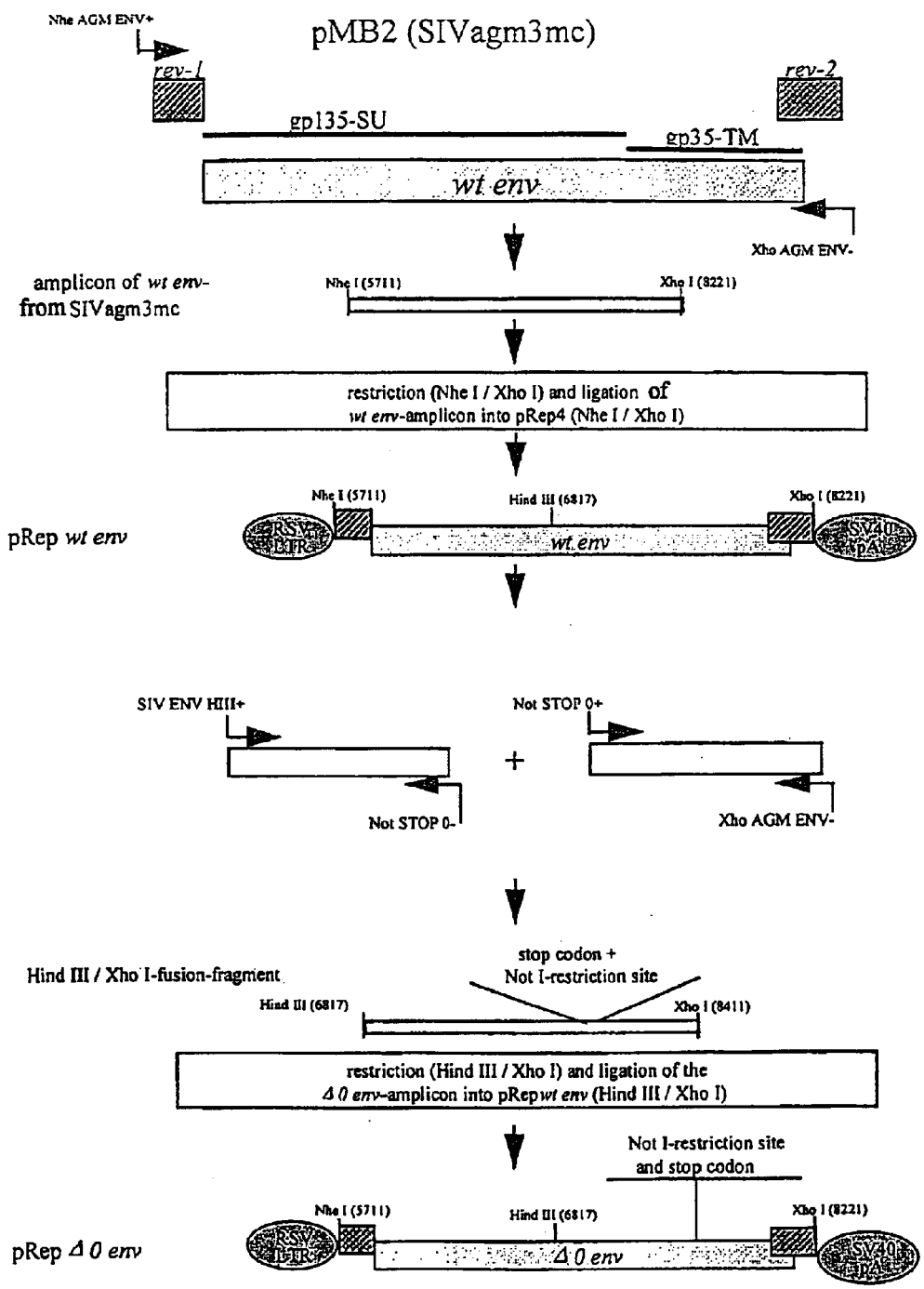
Figure 9:
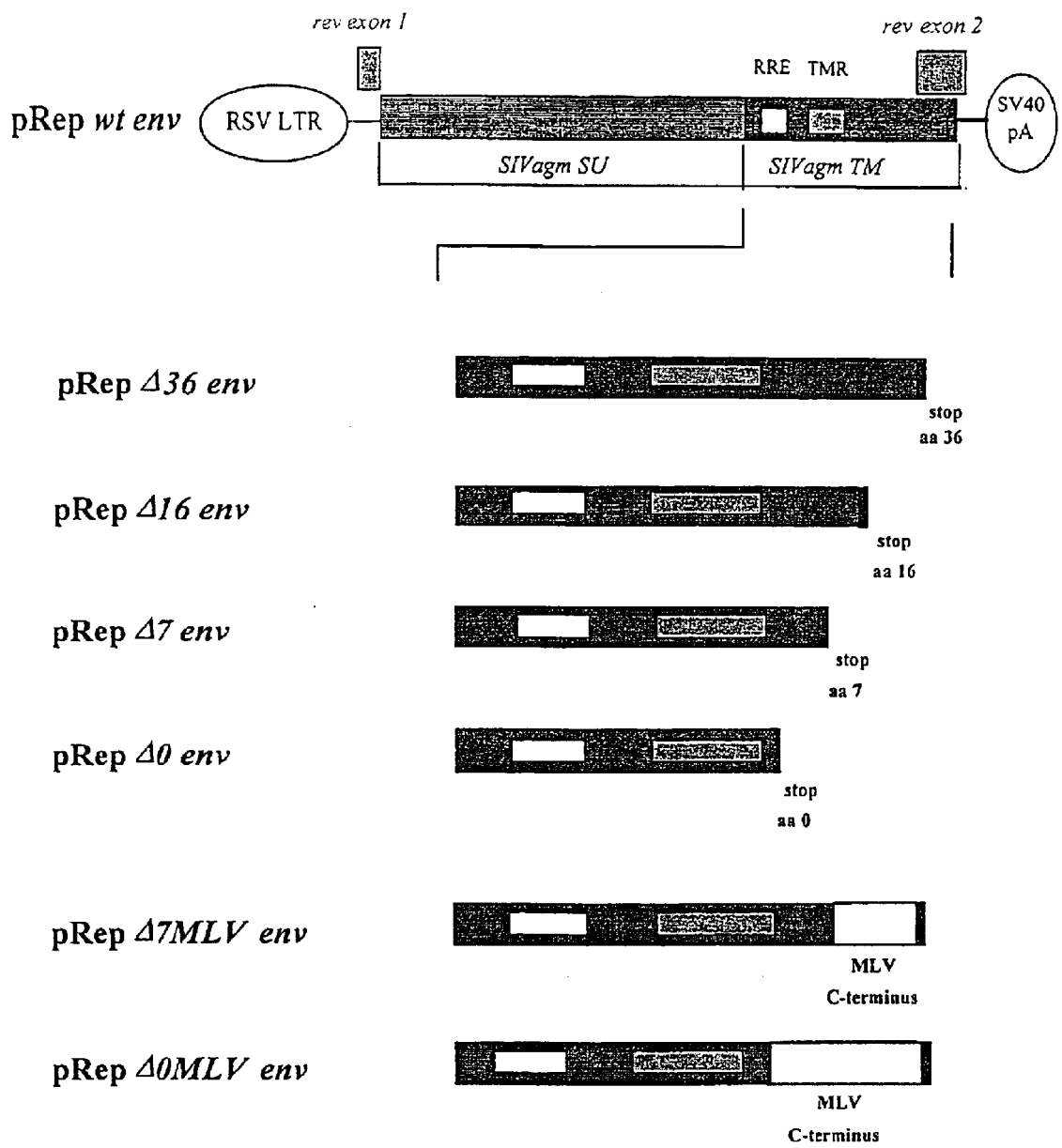
FIG. 9 shows schematically the transcriptional units of the SIVagm3-derived env constructs.
Figure 11:
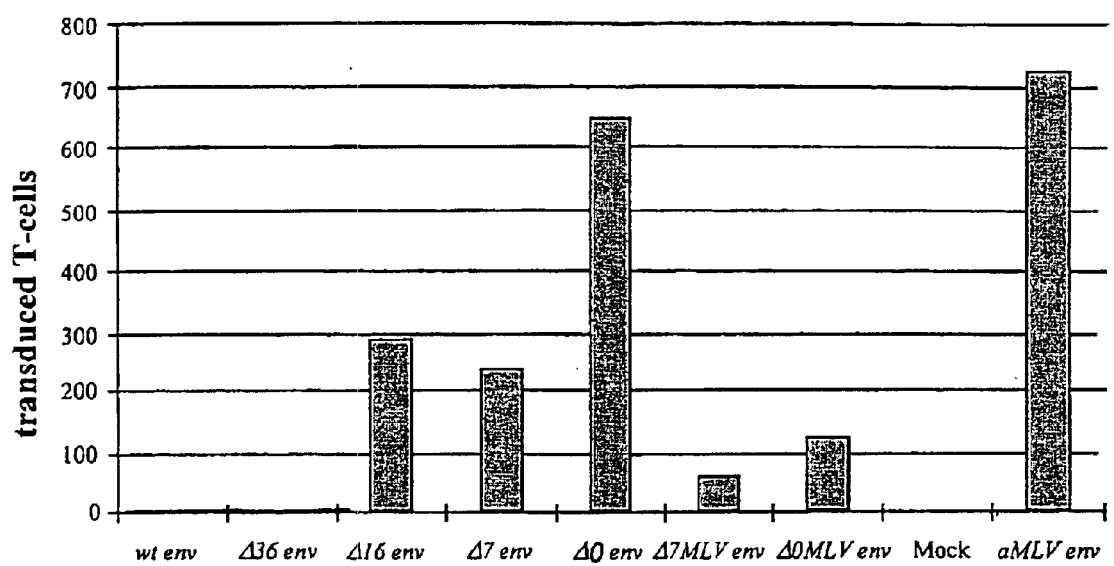

FIG. 11 is a graphic illustration of the efficiency of generation of MLV(SIVagm) vectors upon transfection of the env gene variants into TELCeB6/rev cells. The T-cells were co-cultivated in the same medium and in the presence of the transfected packaging cells for two days and then tested for the successful gene transfer by X-gal staining. The indicated values are mean values resulting from two experiments. "Mock" stands for negative control.

Figure 12:
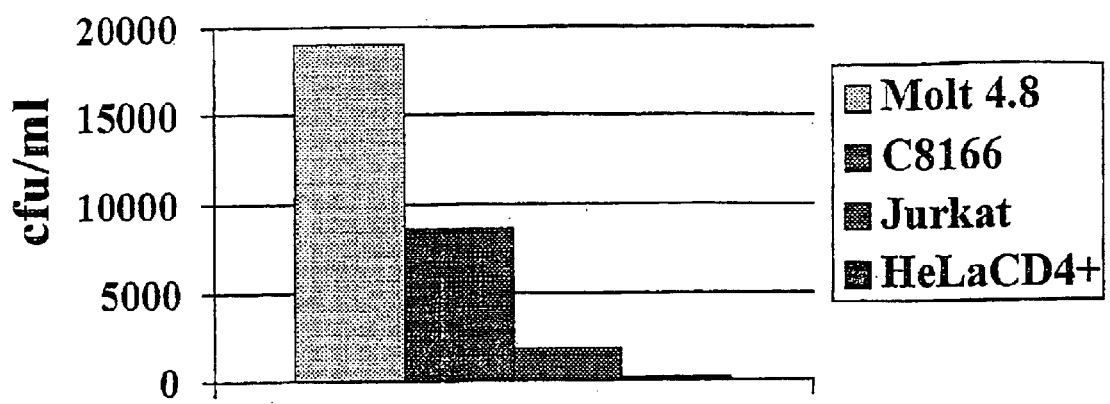

FIG. 12 is a graphic illustration of the results of titration experiments performed with MLV(SIVagm) vector stocks in different CD4-positive cell lines.

Figure 13:
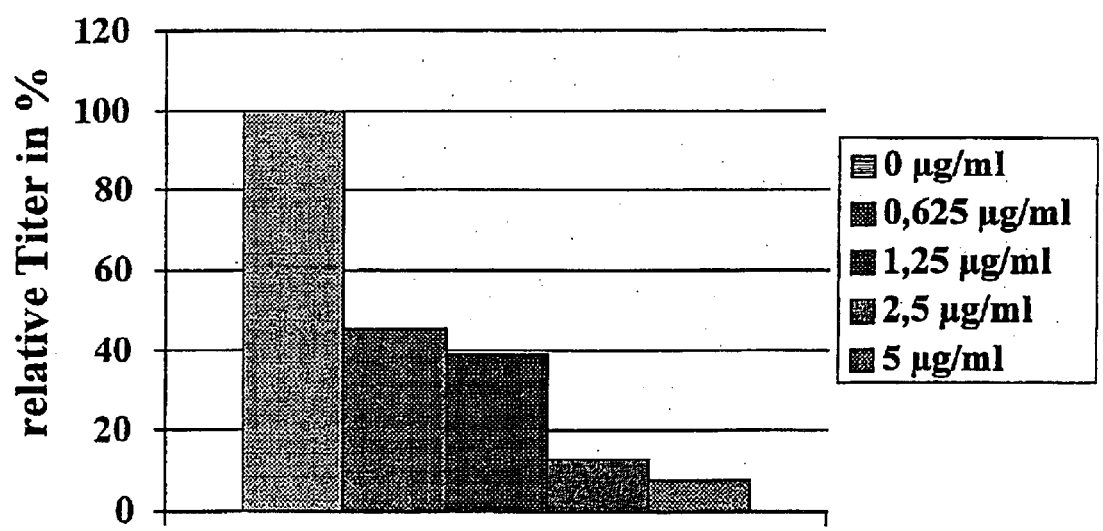

FIG. 13 shows the results of the inhibition of T-cell transduction employing a monoclonal antibody directed against CD4 blocking the cellular CD4-receptor. The concentration of the antibody IOT4a is given in the legend. The transduction efficiency in the absence of the antibody was set as a reverence of 100% and the titers in presence of the antibody is expressed in percent of this positive control.

DETAILED DESCRIPTION

The term "retroviral vector" as used herein, refers to a replication incompetent retroviral particle that is mediating the transfer of a mRNA of a foreign gene, e.g. of a therapeutical gene or of a fragment thereof or of a reporter gene instead of the retroviral mRNA. The term "therapeutical gene" as used herein refers to a nucleic acid sequence that is intended to be transferred into a target cell by a retroviral vector and comprises complete genes, fragments thereof or antisense-nucleic acid sequences. The term "SIV" as used herein refers to viruses of the simian immunodeficiency virus family, e.g. Cerecopithecus aethiops (SIVagm), Macaca mulatta (SIVmac), Pan troglodydytes (SIVcpz), Cerecopithecus mitis (SIVsyk), Papio sphinx (SIVmnd), Cercocebus atys (SIVsm) or Maccaca nemestrina (SIVmne). The term "SIVagm3" as used herein refers to the molecular clone SIVagm3mc (Baier et al., *J. Virol.* 62 (1989), 4123–4128).

The preparation of MLV(HIV-1) and MLV(SIVagm3) vectors is described in detail below.

First, a DNA-sequence is generated that allows the production of the necessary proteins that allow the assembly of the viral core particles. The DNA-sequence is transfected into a human host cell and expressed therein. This DNA-sequence contains additionally operator-elements that are needed to express the DNA-sequence and induce formation of the viral core particles. The new host cell generated that way is then transfected with another DNA-sequence encoding the envelope proteins derived from a virus which is different to the virus from which the viral core particles derived from. Then a third DNA-sequence is transfected into these cells that is packaged by the core particles and that comprises sequences that result in production of the therapeutical gene sequences or desired proteins in the cell into which therapeutical genes are to be transferred by the retroviral vector. The DNA-sequence that result in the expression of the viral envelope proteins can preferably be derived from the env gene of HIV-1 or HIV-2 or other HIV-strains or of SIV, e.g. Cerecopithecus aethiops (SIVagm), Macaca mulatta (SIVmac), Pan troglodydytes (SIVcpz), Cerecopithecus mitis (SIVsyk), Papio sphinx (SIVmnd), Cercocebus atys (SIVsm) or Maccaca nemestrina (SIVmne)). The env genes employed can be equivalent to the original native version of the viruses named above or can be truncated or even further modified variants of the respective env genes. The especially preferred HIV-1 env gene pTr712 results in the generation of a full-length surface envelope protein gp120-SU and a truncated variant of the transmembrane protein. The particularly preferred SIVagm3 env-gene Δ0env results in the generation of a full-length surface envelope protein gp130-SV and a truncated transmembrane protein. The transmembrane protein can be further modified e.g. by fusion of the C-terminal domain or any other fragment of the transmembrane protein derived from MLV or any other virus. For example using core particles derived from MLV one can substitute the C-terminus of the env gene HIV or SIV env gene by the C-terminus derived from the transmembrane protein of MLV. In this case the proteolytic cleavage site of the C-terminal p2 peptide can be modified or not.

The mentioned viral vectors according to the invention can be used for the transfer of therapeutic genes into particular cell types. For example, the MLV(HIV-1) and MLV(SIVagm3) vectors of the invention transfer genes selectively into CD4-positive cells. Thus, these vectors show the tropism of HIV-1 and SIVagm3, respectively, from which the envelope proteins were derived.

EXAMPLES

The following not-limiting examples illustrate the invention.

1. Example 1

Preparation of MLV(HIV-1) Vectors

1.1 Cell Lines and Plasmids

All plasmids used were prepared from transformed *E. coli* strains DH10αor HB101. The molecular cloning of the expression constructs pLβAc/env-neo is described by Kräuslich et al., *Virology* 192 (1993), 605–617 and pLssAc/env-Tr712-neo is described by Kräuslich et al., *Virology* 192 (1993), 605–617 and Wilk et al., *Virology* 189 (1992), 167–177. These expression constructs encode the env gene variants of HIV-1 and the neomycin-resistance gene. The expression construct pCRUCA comprising the env gene of amphotropic MLV is described by Wilk et al., *Virology* 189 (1992), 167–177 and Battini et al., *J. Virol.* 66 (1992), 1468–1475. The TELCeB6 packaging cell line expressing the expression construct pMFG-nlslacZ and the genes gag and pol of MLV is described by Cosset et al., *J. Virol.* 69 (1995), 7430–7436. The cell line HeLaCD4+ was provided by the MRC AIDS reagents depository and 293 cells were purchased from ATCC (ATCC CRL 1573). All adherent cell lines were cultured in Dulbecco's Modified Eagles Medium (GIBCO/BRL, Eggenstein, Germany) supplemented with 10% fetal calf serum.

The human T-cell line Molt4 (ATCC CRL 1582) was kept in RPMI-1640-Medium (GIBCO/BRL, Eggenstein, Germany) supplemented with 10% FCS. The transfection of the packaging cell line TELCeB6 with the expression construct pTr712 was performed using Lipofectamin (GIBCO/BRL, Eggenstein, Germany) according to the manufacturer's instruction. After transfection of the plasmid pRep 4 (Invitrogen, Leek, Netherlands) hygromycine B-selection was performed in the presence of 200 mg/ml hygromycine B (Sigma, Deisenhofen, Germany). One cell clone generated by this protocol is the cell line TELCeB6/pTr712-K14.

1.2 Viral Infections, Determination of Titers and Neutralisation Experiments

The adherent cells were seeded into 24-well plates at a density of $4\times10^4$ cells per well or in 6-well-plates at a density of $2\times10^5$ cells per well. Molt4 cells were seeded at a density of $8\times10^5$ cells per well in a 6-well plates. Prior to infection the cells were incubated over night in cell culture medium. Cells were infected by co-incubation with 1 ml diluted or undiluted retroviral particle containing supernatants for three hours. Virion containing supernatants were freed from contaminating cells by filtration through a 0.45 μm filter. Two days post infection target cells were assayed for the expression of β-Gal by X-gal staining. The viral titers were determined as described. The titers are given in colony forming units per ml (cfu/ml). A serum from a HIV-1-infected donor was employed to neutralize the pseudotyped vectors.

1.3 Immuno-Staining of Transfected Cells

TELCeB6 cells transfected with plasmid-DNA encoding the envelope proteins of HIV-1 were washed with PBS and incubated with ice-cold methanol for 15 min. After repeated washing the cells were incubated with blocking buffer (PBS/2% BSA) for one hour. After repeatedly washing with PBS cells were incubated with a 1:1000 diluted HIV-1 specific serum solution for one hour. Cells were incubated with peroxidase-conjugated protein G (Bio-Rad, Krefeld, Germany). Finally, antigen-presenting cells were stained by addition of substrate-buffer ($H_2O_2$ with 3-amino-9-ethylcarbazol, Sigma, Deisenhofen, Germany). It was demonstrated that the plasmid pTr712 allows the expression of envelope proteins derived from HIV-1 in the transfected cells.

1.4 Western-Blot-Analysis

The preparation of cell lysates and Western-Blotting was performed using standard protocols. Virus particles present in the supernatants of packaging cells transfected with plasmids encoding HIV-1-derived envelope proteins were concentrated by ultracentrifugation (45 min at 200,000×g at 40° C.). The resulting pellets were resolved in sample buffer and subjected to SDS-PAGE. A goat serum directed against HIV-1 gp120-SU and peroxidase conjugated protein G was used for Western-Blotting. Protein bands were visualized using the ECL-detection kit (Amersham, Braunschweig, Germany). The surface envelope protein gp120-SU of HIV-1 was detectable in cell lysates and vector particles.

1.5 Membrane Fusion Capacity of the HIV-1 Envelope Protein

A subconfluent culture of the packaging cell line TELCeB6/pTr712-K14 was covered with Jurkat T-cells, expanded for 48 hours and photographed. A number of syncytia were observed, clearly indicating the functionality of envelope proteins of HIV-1 produced by the cell line mentioned above.

Example 2

Preparation of MLV(SIVagm3) Vectors 2.1 Cloning of the SIVagm3 Env-Expression Constructs The plasmid pRep 4 (Invitrogen, Leek, Netherlands) was used to clone the env gene variants of SIVagm3. To generate the env gene variants the sequence between base 5713 and 8411 of SIVagm3 was amplified from the plasmid pMB2 (Baier et al., *J. Virol.* 63 (1989), 5119–5123) by recombinant PCR (rPCR) using the oligonucleotids Nhe AGM ENV+ (SEQ ID NO: 1) and Xho AGM ENV− (SEQ ID NO:2), and inserted into the plasmid pRep4 via the restriction sites Nhe I and Xho I. The cDNA generated by rPCR encompasses both rev-exons and the complete reading frame of the env gene. The resulting plasmid termed pRep wt env was used as a template for further rPCRs and as a vector for further cloning steps.

Next, the truncated env gene variants Δ0env, Δ7env and Δ16 env were cloned. For this purpose, the respective oligo-nucleotides Not STOP 0−/+ (0+: SEQ ID NO:3, 0+−:SEQ ID NO:4), Not STOP 7−/+ (7−: SEQ ID NO:5, 7+:SEQ ID NO:6) and Not STOP 16−/+ (16−: SEQ ID NO:7, 16+:SEQ ID NO:8) were employed in PCRs to insert the desired stop-codon and the 5'-located Not I-restriction site. To minimize the risk of faulty amplification by the Taq-polymerase small fragments were amplified using the flanking oligo-nucleotides SIV ENV HIII+ (SEQ ID NO:9) and Xho AGM ENV− (SEQ ID NO:2). The resulting fragments (amplicon SEQ ID NO:9/3 together with amplicon SEQ ID NO:4/2, amplicon SEQ ID NO:9/5 with amplicon SEQ ID NO: 6/2, amplicon SEQ ID NO:9/7 with amplicon SEQ ID NO:8/2) were then isolated according to standard protocols and subjected to fusion-PCR. The first amplicon encompasses the sequences derived from SIVagm env from the Hind III-restriction site (nt 6817) to the −primer (Not STOP 0−/7−/16−) that includes the Not I-restriction site and the stop codon to be inserted as well as the 3'-following sequences of the template. The second amplicon begins with the +Primer (Not STOP 0+/7+/16+) encompassing the last bases at the 3' end from the first amplicon, a Not I-restriction site and the stop codon. This amplicon ends with the sequence of the primer Xho AGM ENV−. Thus, the amplicons subjected to the fusion-PCR included overlapping sequences that allowed hybridisation. Using fusion-PCR these amplicons where amplified upon hybridisation employing the primers Xho AGM ENV− and SIV ENV HIII+. The resulting fusion fragments were then digested (Hind III/Xho I) and inserted into the vector Rep wt env (Hind III/Xho I). The env variants Δ0MLVenv and Δ7MLVenv were derived from the variants Δ0 env and Δ7 env. For this purpose, the 3'-laying regions of the MLV env gene encoding the intracellular portions of TM protein p15 were amplified by rPCR using the oligonucleotides MLV Not– (SEQ ID NO: 10) and MLV Not 7+ (SEQ ID NO: 11) or MLV Not 0+ (SEQ ID NO:12), respectively. The molecular clone pKA1558 has been described by Scov et al.,*J. Gen. Virol.* 74 (1993), 707–714 and served as the template. The resulting amplicons were inserted into the env variants Δ0 env or Δ7 env via the Not I-restriction site.

2.2 Polymerase Chain Reaction (PCR)

The Taq-DNA-polymerase (Perkin-Elmer, Langen, Germany) was used for amplification of DNA sequences. A standard-PCR (100 µl total volume) included: 1×PCR-buffer (10 mM Tris/HCl, pH 8.8, 50 mM KCl, 1.5 mM $MgCl_2$, 0.01% gelantine), 10 µM of each amplicon, 2 µM of the respective oligodeoxynucleotide-primers, 200 µM of each deoxynucleotide (dNTP), 2.5 units of the Taq-polymerase and 100 ng plasmid-DNA. The PCR-program using the primer pairs of amplicon SEQ ID NO: 9/3 with amplicon SEQ ID NO: 4/2, amplicon SEQ ID NO: 9/5 with amplicon SEQ ID NO: 6/2 and amplicon SEQ ID NO: 9/7 with amplicon SEQ ID NO: 8/2 was as follows:

1. 94° C. 300 sec.
2. 94° C. 45 sec.
3. 55° C. 120 sec
4. 72° C. 180+2 sec.
5. 10 cycles 2.–4.
6. 94° C. 45 sec.
7. 60° C. 120 sec.
8. 72° C. 180+2 sec.
9. 10 cycles 6.–8.
10. 72° C. 600 sec.

2.3 Cell Lines, Media, Transformation and Transfection

Plasmids were transformed into *E. coli*-strains DH5α, DH10B, Top10F'(GIBCO/BRL, Eggenstein, Germany) and GM 2163 (Invitrogen, Leek, Netherlands) using standard methods. The transfection of the packaging cells TELCeB6 and TELCeB6/rev with the SVagm env gene expression constructs were performed using Lipofectamin (GIBCO/BRL, Eggenstein, Germany) according to the manufacturer's instructions. The packaging cell line TELCeB6 expressing the retroviral expression construct MFG-nlsLacZ and the gag/pol genes of MLV has been described by Cosset et al., *J. Virol.* 69 (1995), 7430–7436. Cell line TELCeB6/rev was stably transfected with the construct pCMV-rev (NIH Research and Reference Reagent Program, catalogue no. 1443) allowing the expression of the rev gene of HIV-1 under the transcriptional control of a CMV-promotor. Thus, the resulting cell line TELCeB6/rev expresses in addition the rev gene of HIV-1. The cell lines TELCeB6 and TELCeB6/rev were cultured in the media described below for the cultivation of adherent cells supplemented with glucose (4 g/L). Adherent HeLaCD4+cells were purchased from the MRC AIDS Program Reagents Project and the HeLa cells were purchased from ATCC(CCL 2). All adherent cells lines cultivated in Dulbecco's Modified Eagles Medium (GIBCO/BRL, Eggenstein; Germany) supplemented with 10% inactivated fetal calf serum (FCS; Biochrom KG, Berlin, Germany), 2 mM L-glutamine (Biochrom KG, Berlin, Germany) and antibiotics (0.1 mg/ml nystatin, 100 units/ml penicillin, 50 mg/ml streptomycin, Biochrom KG, Berlin, Germany) at 37° C., 5% $CO_2$ and water-saturated athmosphere in a cell incubator (Cytoperm, Heraeus, Germany). The suspension cells C8166 (human leukemia T-cell line containing the defective HTLV-1 genome, NIH Research and Reference Reagent Program, catalogue no. 404), Jurkat cells (human leukemia T-cells, NIH Research and Reference Reagent Program, catalogue no. 177) and Molt4 (human leukemia T-cells, NIH Research and Reference Reagent Program, catalogue no. 175) were kept in RPMI 1640 (GIBCO/BRL, Eggenstein, Germany) supplemented with 10% FCS, 2 mM L-glutamine (Biochrom KG, Berlin, Germany) and antibiotics (0.1 mg/ml nystatin, 100 units/ml penicillin, 50 mg/ml streptomycin, Biochrom KG, Berlin, Germany).

2.4 Immuno-Peroxidase-Assay Anti-Peroxidase (IPAP)

To test the correct expression of the env gene variants all env encoding constructs were transfected into TELCeB6 cells. Two days post transfection the transfected cells were tested for the expression of the respective env variant using IPAP. The transfected TELCeB6 cells seeded in 35 mm-tissue culture plates were washed with PBS and ice cold methanol (−20° C.) was added and incubated for 15 min at −20° C. for fixation. Then cells were washed again with PBS and unspecific binding sites were saturated by incubation with blocking buffer (PBS+2% BSA) at room temperature (RT) for one hour. Subsequently, cells were incubated with an anti-serum directed against SIVagm taken from an pig-tail macaque (Macaca nemestrina) infected with SIVagm. This serum was diluted in blocking buffer and was incubated with the cells for one hour at 37° C. After repeated washing with PBS the Fc-portions of the primary antibodies were detected using horseradish-peroxidase-conjugated protein G (BIO-RAD, Munich, Germany) after incubation for one hour at 37° C. After washing the cells twice with PBS substrate buffer (4 mg 3-Amino-9-ethylcarbazol solved in 1 ml dimethylformamid, 19 ml 20 mM NaOAc-buffer, pH 5 and 30 $\mu$l $H_2O_2$; cleared by filtration through a 0.45 $\mu$m filter) was added. After a few minutes of incubation at RT cells expressing viral proteins clearly stained red. With the exception of the plasmids pRep Δ7env and pRep Δ7MLVenv, all other constructs mediated expression of the envelope proteins derived from SIVagm3. The analysis of the sequencing data revealed a stop codon in the second rev-exon in the two variants pRep Δ7env and pRep Δ7MLVenv resulting from the insertion of the Not I-restriction site. Thus, the incompletely produced Rev-protein was not able to mediate the export of the mRNA-transcripts of the env genes from the cell nucleus.

2.5 Syncytia-Formation

As the IPAP analysis only allows the demonstration of the expression of the envelope proteins their functionality had to be tested as well. Using a syncytia-formation test it was intended to show that the envelope proteins were present on the cell surface and able to induce syncytia-formation in CD4+ cells. For that purpose, the SIVagm-derived env gene constructs were transfected into TELCeB6/rev cells. At the following day, the transfected cells were covered by Molt4 T-cells and photographed 24 h later. The SIVagm-derived envelope proteins presented on the cell surface of the packaging cells are able to bind to the CD4-proteins present on the membrane of the T-cells. Thus, fusion of the two cell types occurs. These syncytias are distinguishable from the parental cells by their size. All tested env gene variants induced syncytia-formation, but were very different in the extent of inducing syncytia-formation. Whereas the variants Δ0env and Δ16env induced large syncytia the other variants including wt env mediated only weak syncytia induction. Nevertheless, it was demonstrated for all variants that their expression resulted in the production of membrane proteins able to bind CD4.

2.6 Detection of β-galactosidase Activity (X-gal-Assay)

The successful transduction of human cells mediated by [MLV(SIVagm)] derived vectors was demonstrated by the detection of the successful gene transfer of the packageable construct MFG-nlsLacZ tested by X-gal-assay. The detection of β-galactosidase activity in transduced cells was performed using a modified protocol of the X-Gal-assay (Sanes et al., *EMBO J* 5 (1986), 3133–3142). The reaction buffer contained β-galactosidase substrate (5-brom 4chlor-indodyl-β-D-galactopyranosid; Sigma, Deisenhofen; Germany) [1 mg/ml], 5 mM potassium-ferricyanid (Sigma, Deisenhofen, Germany), 5 mM potassium-ferrocyanid (Sigma, Deisenhofen, Germany) and 2 mM $MgCl_2$ in PBS. The cells were washed with PBS and incubated for 10 min at RT in PBS, 2% formaldehyde and 0.2% glutaric dialdehyde. Then, cells were washed with PBS and incubated with the X-Gal reaction buffer for 5–24 h at 37° C. β-galactosidase activity was demonstrated by intracellular blue staining.

2.7 Transduction of T-cells by [MLV(SIVagm3)] Vectors $4 \times 10^5$ TELCeB6/rev cells were seeded in 35-mm tissue culture plates to be transfected 24 h later with the SIVagm-derived env-constructs. The following day, transfected cells were supplemented with fresh media. Then co-cultivation devices (Costar, Cambridge, USA) were installed in the tissue culture plates of the packaging cells allowing the free diffusion of media and vectors contained therein, but preventing direct cell-to-cell contact. $10^6$ Molt4 T-cells were seeded into these co-cultivation devices and expanded for two days in the presence of the respective transfected cells. After further two days of cultivation in the absence of the packaging cells, the T-cells were tested for the expression of the reporter gene LacZ using the X-Gal-assay.

The transfection of all SIVagm-derived env gene variants displaying a intracellular domain of no more than 19 amino acid moieties resulted in the generation of pseudotyped MLV-vectors successfully transducing the T-cells. The variants wt env and Δ36 env did not generate detectable amounts of these vectors. The transfection of the plasmid pHIT 456 encoding the env gene of amphotropic MLV (Soneoka et al., *Nucl. Acid Research* 23 (1995), 628–633) served as a positive control.

Example 3

3.1 Establishment of Stably Transfected Packaging Cell Clones

To prepare high-titer vector stocks TELCeB6 cells were stably transfected with the respective env-constructs and subsequently subjected to selection. The media used for selection correspond to the media used for the cultivation, but included additionally the neomycin analogoue G418 (800 μg/ml) for selection of $neo^+$-cells (HIV-1 env-constructs) or hygromycine B (200 μg/ml) for the selection of $hyg^+$-cells (SIVagm env-constructs). The antibiotics were purchased from Sigma (Deisenhofen, Germany). The selection of transferred cells was started two days post transfection and carried out for further 10 days until cell clones formed colonies. The clonal cells were detached and resuspended from the tissue culture plate using an "Eppendorf-pipette". These single cell clones were first expanded in 24-well tissue culture dishes and tested for the generation of vectors by titration in suitable target cells.

3.2 Generation of Pseudotyped MLV-Vectors

The vectors produced by the packaging cells were prepared as follows: The media of confluent packaging cultures in large tissue culture flasks (800 ml) were substituted by 15 ml of fresh medium and cells were incubated over night. Then the supernatants were freed from contaminating cells by passaging through a 0.45 μm filter and either subsequently subjected to transduction or stored in liquid nitrogen.

3.3 Determination of Vector Titers

To evaluate the vector amounts in the supernatants of the packaging cells, various dilutions of these supernatants in fresh culture media were prepared in a total volume of 1 ml and subjected to transduction of permissive target cells (Molt4, C8166, Jurkat, HeLaCD4+). The dilutions employed were 1:1, 1:10, 1:100, 1:1000. The adherent HeLaCD4+ target cells were seeded at a density of $2 \times 10^5$ cells per 35 mm-tissue culture plate one day prior to transduction. The cells were washed with PBS before incubation for two hours at 37° C. in the presence of the vector containing media. Then, cells were washed again with PBS and expanded for further two days before the transduced cells were visualized by staining using the X-gal-assay. Suspension cells were supplied with fresh media one day prior to transduction. $10^6$ cells were pelleted (by centrifugation) in the usual manner and then directly resuspended in the vector containing dilutions. After two hours these cells were washed and expanded for further two days before the successful gene transfer was detected using the X-gal-assay. The LacZ+ and thus stained cells were counted within 10–20 image-fields using a light microscope (Axiovert 35, Carl Zeiss, Jena, Germany) and the total $LacZ^+$-cell count within the whole tissue culture plate was evaluated by extrapolation. The dilution of the vector containing supernatants was taken into consideration and the titers were expressed in cfu/ml. Molt4 cells were transduced at the highest efficiency, whereas C8166 and Jurkat T-cell lines were considerably less efficiently transduced. HeLaCD4+ cells seem to be hardly permissive for [MLV (SIVagm)] vectors. In contrast the [MLV(HIV-1)] vectors enabled efficient transduction of all CD4+ cell lines tested.

Example 4

Demonstration of the CD4-Dependent Transduction Mediated by [MLV(SIVagm)] Vectors 30 min prior to transduction by [MLV(SIVagm)] vectors Molt4 T-cell line was incubated in media containing various concentrations (0 μg/ml, 0.625 μg/ml, 1.25 μg/ml, 2.5 μg/ml, 5 μg/ml) of the monoclonal antibody IOT4a (Dianova, Hamburg, Germany) directed against CD4. This antibody inhibits the entry of different HIV- and SIV-isolates by blocking the cellular receptor CD4 (Sattentau et al., *Science* 234 (1986), 1120–1127). The T-cells were transduced by [MLV(SIVagm)] vectors in the presence of the concentrations of the anti-CD4-antibody IOT4a mentioned above. Then cells were washed and expanded for further two days before the resulting gen transfer was measured using the X-gal-assay. Cells transduced in the absence of the antibody served as positive controls and were chosen as a reference (100%). It was clearly shown that the efficiency of gene transfer correlated depending on the concentration of the antibody added.

Other Embodiments

Other aspects, advantages, and modifications of the invention are within the scope of the following claims.

What is claimed is:

1. A retroviral vector comprising
   a viral core of murine leukemia virus (MLV); and
   a virus envelope comprising a full-length surface envelope protein of human immunodeficiency virus (HIV) or simian immunodeficiency virus (SIV) and a truncated transmembrane envelope protein of HIV or SIV.

2. The retroviral vector of claim 1, wherein the truncated transmembrane envelope protein is an HIV truncated transmembrane envelope protein.

3. The retroviral vector of claim 1, wherein (a) the full-length surface envelope protein is an HIV type 1 or an HIV type 2 surface envelope protein and (b) the transmembrane envelope protein is an HIV type 1 or an HIV type 2 transmembrane envelope protein.

4. The retroviral vector of claim 1, wherein the C-terminus of a truncated transmembrane envelope protein of HIV or SIV is fused to a fragment of an MLV transmembrane envelope protein.

5. A composition comprising the retroviral vector of claim 1, wherein the retroviral vector further comprises a therapeutic gene, a reporter gene, or a biologically active fragment of a therapeutic gene or reporter gene, wherein the vector mediates the transfer of the therapeutic gene, the reporter gene, or the fragment of the therapeutic gene or reporter gene into a CD4-positive cell of a mammal.

6. The composition of claim 5, wherein the CD4-positive cell is a human cell.

7. A composition comprising a retroviral vector of claim 1, wherein the vector further comprises a foreign gene or a fragment thereof.

8. The composition of claim 7, wherein the CD4-positive cell is a human cell.

9. The retroviral vector of claim 1, wherein the SIV surface envelope protein is an SIV surface envelope of Cerecopithecus aethiops (SIVagm), Macaca mulatta (SIVmac), Pan troglodydytes (SIVcpz), Cerecopithecus mitis (SIVsyk), Papio sphinx (SIVmnd), Cercocebus atys (SIVsm), or Macaca nemestrina (SIVmne), and the SIV transmembrane envelope protein is an SIV transmembrane envelope of Cerecopithecus aethiops (SIVagm), Macaca mulatta (SIVmac), Pan troglodydytes (SIVcpz), Cerecopithecus mitis (SIVsyk), Papio sphinx (SIVmnd), Cercocebus atys (SIVsm), or Macaca nemestrina (SIVmne).

10. The retroviral vector of claim 1, wherein the full-length surface envelope protein is an HIV protein and the truncated transmembrane envelope protein is an HIV protein.

11. The retroviral vector of claim 10 wherein the HIV is HIV type 1.

12. The retroviral vector of claim 10, wherein the HIV is HIV type 2.

13. The retroviral vector of claim 1, wherein the full-length surface envelope protein is an SIV protein and the truncated transmembrane envelope protein is and SIV protein.

14. A method for preparing a packaging cell that produces a retroviral vector, the method comprising transfecting a cell with
   (i) a psi-negative expression construct comprising a gag gene and apol gene of murine leukemia virus (MLV);
   (ii) a psi-positive expression construct encoding a desired gene product; and
   (iii) a transcriptional cassette encoding an envelope protein of human immunodeficiency virus (HIV) or simian immunodeficiency virus (SIV), thereby generating a packaging cell that produces a retroviral vector comprising a viral core of MLV and a virus envelope comprising an envelope protein of HIV or SIV.

15. A packaging cell prepared by the method of claim 14.

16. A method for preparing a packaging cell that produces a retroviral vector, the method comprising:
   obtaining a cell of a packaging cell line comprising a gag-gene and apol-gene of murine leukemia virus (MLV) and an expression construct encoding a therapeutic gene, a reporter gene, or a biologically active fragment of a therapeutic or reporter gene; and
   transfecting the cell of the packaging cell line with a construct comprising a transcriptional cassette encoding an envelope protein of human immunodeficiency virus (HIV) or simian immunodeficiency virus (SIV), thereby generating a packaging cell that produces a retroviral vector comprising a viral core of MLV and a virus envelope comprising an envelope protein of HIV or SIV.

* * * * *

UNITED STATES PATENT AND TRADEMARK OFFICE
CERTIFICATE OF CORRECTION

| | | |
|---|---|---|
| PATENT NO. | : 6,902,929 B1 | Page 1 of 1 |
| APPLICATION NO. | : 09/380324 | |
| DATED | : June 7, 2005 | |
| INVENTOR(S) | : Klaus Cichutek et al. | |

It is certified that error appears in the above-identified patent and that said Letters Patent is hereby corrected as shown below:

Title Page, Section (87) PCT Pub. No.: replace "WO98/38825" with -- WO98/38325 --.

Signed and Sealed this

Nineteenth Day of February, 2008

JON W. DUDAS
*Director of the United States Patent and Trademark Office*